US006255544B1

(12) United States Patent
Sievert

(10) Patent No.: US 6,255,544 B1
(45) Date of Patent: Jul. 3, 2001

(54) PROCESS FOR THE MANUFACTURE OF HALOCARBONS

(75) Inventor: Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/341,616

(22) PCT Filed: Jan. 7, 1998

(86) PCT No.: PCT/US98/00579

§ 371 Date: Jul. 13, 1999

§ 102(e) Date: Jul. 13, 1999

(87) PCT Pub. No.: WO98/31649

PCT Pub. Date: Jul. 23, 1998

Related U.S. Application Data

(60) Provisional application No. 60/035,383, filed on Jan. 16, 1997.

(51) Int. Cl.$^7$ ................................................ C07C 17/06
(52) U.S. Cl. ......................... 570/181; 570/247; 570/261
(58) Field of Search .......................... 570/134, 135, 570/167, 172, 156, 181, 247, 261

(56) References Cited

U.S. PATENT DOCUMENTS

| 3,651,019 | 3/1972 | Asscher et al. ................ 260/77.2 |
| 5,414,165 | 5/1995 | Nappa et al. ................ 570/169 |

FOREIGN PATENT DOCUMENTS

| 0 522 639A1 | 1/1993 | (EP) | ................ C07C/19/08 |
| 2 073 533 | 1/1993 | (CA) | ................ C07C/19/08 |
| WO 95/04022 | 2/1995 | (WO) | ................ C07C/17/23 |
| WO 97/05089 | 2/1997 | (WO) | ................ C07C/17/278 |
| WO 97/05090 | 2/1997 | (WO) | ................ C07C/17/278 |

OTHER PUBLICATIONS

M. Belbachir et al., Telomerisation du chlorue de vinylidene, 1. Reaction avec le tetrachlorurer de carbone par catalyse redox, *Makromolekulare Chemie*, 185, No. 8, 1583–1595, 1984 (with translation).

M. Kotora et al. Elsevier Science Publishers, *Addition of tetrachloromethane to halogenated ethenes catalyzed by transition metal complexes*, 77, pp. 51–60, 1992.

M. Kotora et al., React. Kinet. Catal. Lett., *Selective additions of polyhalogenated compounds to chloro substituted ethenes catalyzed by a copper complex*, vol. 44, No. 2, pp. 415–419, 1991.

*Primary Examiner*—Floyd D. Higel
*Assistant Examiner*—Ebenezer Sackey

(57) ABSTRACT

A liquid phase process is disclosed for producing halogenated alkane adducts of the formula $CAR^1R^2CBR^3R^4$ (where A, B, $R^1$, $R^2$, $R^3$, and $R^4$ are as defined in the specification) which involves contacting a corresponding halogenated alkane, AB, with a corresponding olefin, $CR^1R^2{=}CR^3R^4$ in a solvent and in the presence of a catalyst system containing (i) at least one catalyst comprising monovalent copper, and (ii) at least one ionic promoter selected from the group consisting of substituted ammonium halides, pyridinium and substituted pyridinium halides, and quaternary salts of the type $(MQ_4)Y$ where M is an element of Group VA of the Periodic Table (i.e., N, P, As, Sb, or Bi), Q is a $C_1$–$C_{18}$ hydrocarbyl group, and Y is chloride, bromide or iodide. Production of hydrofluoroalkanes by reacting selected adducts of the type produced above with HF is also disclosed.

7 Claims, No Drawings

US 6,255,544 B1

PROCESS FOR THE MANUFACTURE OF HALOCARBONS

This application is a 371 of PCT/US98/00579 filed Jan. 7, 1998 which claims priority to provisional application Ser. No. 60/035,383 filed Jan. 16, 1997.

FIELD OF THE INVENTION

This invention relates to a process for the manufacture of halogenated alkanes using the catalytic reaction of haloalkanes with halogenated olefins.

BACKGROUND

The catalyzed radical addition of haloalkanes to olefins is a well known reaction. Typically, however, when a haloalkane (e.g., AB, where A is a substituted carbon atom and B is a halogen other than fluorine) is added to an olefin (e.g., $CH_2=CHR$) to form the saturated adduct (e.g., $CH_2ACHBR$), the products (i.e., halogenated addition compounds) also include varying amounts of telomers (e.g., $A(CH_2CHR)_nB$, where n is equal to 2 or more). For example, Canadian Patent No. 2,073,533 discloses a process for the manufacture of $CCl_3CH_2CCl_3$ by reacting carbon tetrachloride with vinylidene chloride using copper catalysts in acetonitrile. The selectivity for $CCl_3CH_2CCl_3$ with respect to converted vinylidene chloride was 87%. It has been shown in the art that the major by-product is the $C_5$ telomer, $CCl_3(CH_2CCl_2)_2Cl$. Furthermore, since the catalyzed addition of haloalkanes to olefins is done in a homogeneous medium, separation of the catalyst from the product can present difficulties. This is especially so when it is desired to run the reaction in a continuous manner.

The halogenated adducts are useful intermediates for the production of fluoroalkanes, particularly, hydrofluoroalkanes. These latter compounds are useful as refrigerants, fire extinguishants, heat transfer media, propellants, foaming agents, gaseous dielectrics, sterilant carriers, polymerization media, particulate removal fluids, carrier fluids, buffing abrasive agents, displacement drying agents and power cycle working fluids. There is an interest in developing more efficient processes for the manufacture of hydrofluoroalkanes.

SUMMARY OF THE INVENTION

A liquid phase process is provided in accordance with this invention for producing halogenated alkane adducts of the formula $CAR^1_R{}^2CBR^3R^4$ wherein $R^1$, $R^2$, $R^3$, and $R^4$ are each independently selected from the group consisting of H, Br, Cl, F, $C_1$–$C_6$ alkyl, CN, $CO_2CH_3$, $CH_2Cl$, and aryl (e.g., phenyl), provided that when either $R^3$ or $R^4$ is selected from the group consisting of $C_3$–$C_6$ alkyl, CN, $CO_2CH_3$, $CH_2Cl$, and aryl, then $R^1$, $R^2$, and the other of $R^3$ and $R^4$ are H, and when $R^3$ and $R^4$ are selected from the group consisting of Cl, F, $CH_3$ and $C_2H_5$, then $R^1$ and $R^2$ are H, and when either $R^1$ or $R^2$ and either $R^3$ or $R^4$ are selected from the group consisting of Cl, F, $CH_3$ and $C_2H_5$, then the other of $R^1$ and $R^2$ and the other of $R^3$ and $R^4$ are H; A is selected from the group consisting of $CX_3$, $CH_{3-a}X_a$, $C_nH_{(2n+1)-b}X_b$ and $CH_cX_{2-c}R$, where R is $C_nH_{(2n+1)-b}X_b$ (e.g., $CF_3$ and $CCl_2CF_3$), each X is independently selected from the group consisting of Br, F, Cl and I, a is an integer from 0 to 3, n is an integer from 1 to 6, b is an integer from 1 to 2n+1, and c is an integer from 0 to 1; and B is selected from the group consisting of Br, Cl and I; provided that (1) when A is $CX_3$ then only one of X is I, (2) when A is $CH_{3-a}X_a$, then each X is B and a is 2 when B is Br or Cl, and a is an integer from 0 to 2 when B is I, and (3) when A is $CnH_{(2n+1)-b}X_b$, then each X is independently selected from Cl and F, and B is I. The process comprises contacting a halogenated alkane of the formula AB (where A and B are as indicated above) with an olefin of the formula $CR^1R^2=CR^3R^4$ (where $R^1$, $R^2$, $R^3$ and $R^4$ are as indicated above) in a dinitrile or cyclic carbonate ester solvent which divides the reaction mixture into two liquid phases and in the presence of a catalyst system containing (i) at least one catalyst comprising monovalent copper; (ii) at least one ionic promoter selected from the group consisting of substituted ammonium halides, pyridinium and substituted pyridinium halides, and quaternary salts of the type $(MQ_4)Y$ where M is an element of Group VA of the Periodic Table (i.e., N, P, As, Sb, or Bi), Q is a $C_1$–$C_{18}$ hydrocarbyl group, and Y is Cl, Br or I; and optionally (iii) a non-ionic promoter selected from the group consisting of aromatic or aliphatic non-ionic heterocyclic compounds which contain at least one carbon-nitrogen double bond in the heterocyclic ring.

This invention further provides a process for producing hydrofluoroalkanes (e.g., $CF_3CH_2CHF_2$). This process comprises (a) producing a halogenated alkane adduct (e.g., $CCl_3CH_2CHCl_2$) by reacting AB (e.g., $CCl_4$) and $CR^1R^2=CR^3R^4$ (e.g., $CH_2=CHCl$) as indicated above (provided that $R^1$, $R^2$, $R^3$ and $R^4$ are independently selected from H, $CH_3$, $C_2H_5$, C and F, B and X are Cl and at least one of AB and $CR^1R^2=CR^3R^4$ contains hydrogen), and (b) reacting the adduct produced in (a) with HFP.

DETAILED DESCRIPTION

The present invention relates to the addition of halogenated alkanes to unsaturated compounds to form an adduct. Specifically, this invention relates to the addition of a halogenated alkane of the general formula AB to an unsaturated compound $CR^1R^2=CR^3R^4$ to form a corresponding adduct $CAR^1R^2CBR^3R^4$ in a the presence of a monovalent copper catalyst ($Cu^+$) in a suitable solvent (a dinitrile or cyclic carbonate ester solvent). An ionic promoter is used to enhance the reaction. A second, non-ionic promoter containing a C=N ring bond may also be advantageously used.

The addition of saturated, halogenated alkanes to alkenes to form adducts is known in the art. A wide range of saturated, halogenated alkanes may be used in the process of the invention. Examples of suitable saturated, halogenated alkanes are given by Walling and Huyser in Tables V, VI, VII, and VIII in Chapter 3 of Organic Reactions, Vol. 13 (1963).

Halogenated alkanes, AB, that are particularly useful for the process of this invention include certain compounds where A is selected from the group consisting of $CX_3$, $CH_{3-a}X_a$, $C_nH_{(2n+1)-b}X_b$ and $CH_cX_{2-c}R$ where each X is Br, F, Cl or I and R is $C_nH_{(2n+1)-b}X_b$ (e.g., $CF_3$ and $CCl_2CF_3$); and B is Br, Cl or I. Included are compounds where A is $CX_3$ and only one of X is I. Also included are compounds where A is $CH_{3-a}X_a$ where X is B and where when X is Br or Cl, a is 2, and when X is I, a is an integer from 0 to 2. Also included are the compounds where A is $C_nH_{(2n+1)-b}X_b$, where each X is independently selected from Cl and F, n is an integer from 1 to 6, b is an integer from 1 to 2n+1, and B is I. Also included are compounds where A is $CH_cX_{2-c}R$ wherein c is an integer from 0 to 1. Examples of saturated, halogenated alkanes suitable for the process of this invention include $CCl_4$, $CBrCl_3$, $CCl_2FCCl_2F$, $CCl_3CClF_2$, $CCl_3CF_3$, $CCl_3CF_2CCl_3$, $CCl_3CF_2CF_3$, $CCl_3CH_2CCl_3$, $CCl_3CH_2CF_3$, $CCl_3CF_2CClF_2$, $CF_3I$, $CF_3CF_2I$, $CF_3CFICF_3$ and $CF_3CF_2CF_2I$.

A wide range of alkenes may be used in the process of the invention. Examples of suitable alkenes are given by Walling and Huyser in Tables V, VI, VII, and VIII in Chapter 3 of Organic Reactions, Vol. 13 (1963). Examples of alkenes suitable for the process of this invention include $CH_2=CH_2$, $CH_2=CHCl$, $CH_2=CHF$, $CHCl=CHCl$, $CH_2=CCl_2$, $CH_2=CF_2$, $CH_2=CHCH_3$, $CH_2=CHCH_2Cl$, and $CH_2=CHC_6H_5$.

The addition of halogenated alkanes to alkenes to form the corresponding adducts is catalyzed by copper(I) compounds, that is, copper compounds in the +1 oxidation state. Preferred copper compounds for the process of this invention include copper(I) chloride, copper(I) bromide, copper(I) iodide, copper(I) acetate, and copper(I) thiocyanate. Especially preferred copper compounds for the process of this invention include copper(I) chloride and copper(I) bromide. The catalysts are preferably anhydrous; and preferably, the addition of halogenated alkanes to alkenes is done under substantially anhydrous conditions in the substantial absence of oxygen. Without wishing to be bound by theory, it is believed that the effect of the catalyst is to enhance the yield of the 1:1 addition product (i.e., the adduct) of the halogenated alkanes to the alkene relative to higher molecular weight telomers that are known in the art.

The action of the copper(I) catalyst in the process of the invention is promoted by certain soluble salts. Suitable soluble salts for the process of this invention include substituted ammonium halides, pyridinium and substituted pyridinium halides, and quaternary salts of the type $(MQ_4)Y$ where M is an element of Group VA of the Periodic Table (i.e., N, P, As, Sb, or Bi), Q is independently selected from the group consisting of $C_1$–$C_{18}$ acyclic or cyclic alkyl, benzyl ($CH_2C_6H_5$), phenyl ($C_6H_5$), substituted benzyl, or substituted aryl, and Y is chloride, bromide or iodide. Mixtures of these soluble salts may also be used.

Examples of substituted ammonium halides include HY adducts of alkylamines ($QNH_3Y$), aryl amines ($ArNH_3Y$), dialkylamines ($Q_2NH_2Y$), and trialkylamines ($Q_3NHY$) where Y and Q are as defined above. Specific examples of these types of compounds include ethylamine hydrochloride, benzylamine hydrochloride, anilinium chloride, dimethylamine hydrochloride, piperidine hydrochloride, piperazine dihydrochloride, trimethylamine hydrochloride, triethylamine hydrobromide, and triethylamine hydrochloride.

Examples of pyridinium and substituted pyridinium halides include pyridinium chloride, N-methyl pyridinium bromide, and 1-tetradecyl-3-picolinium chloride.

Examples of quaternary salts of the type $(MQ_4)Y$ where M is an element of Group VA of the Periodic Table (i.e., N, P, As, Sb, or Bi), include quaternary ammonium haldies, $Q_4NY$, where Q and Y are as defined above. Specific examples of quarternary ammonium halides include tetramethylammonium chloride, tetramethylammonium bromide, tetraethylammonium bromide, tetraethylammonium chloride, tetrabutylammonium bromide, tetrabutylammonium chloride, tetra-n-hexylammonium bromide, benzyltrimnethylammonium bromide, tricaprylylmethyl chloride, benzyltributylammonium bromide, dodecyltrimethylammonium bromide, tetra-n-amylammonium chloride, and decamethylenebis(trimethylammonium bromide).

Other examples of quaternary salts of the type $(MQ_4)Y$ include tetraphenylphosphonium chloride, tetraphenylphosphonium bromide, n-hexadecyltributylphosphonium bromide, methyltriphenylphosphonium bromide, and tetraphenylarsonium chloride.

The copper catalyst for the process of the invention may also, if desired, be further promoted by certain heterocyclic non-ionic compounds. Suitable non-ionic promoters include those selected from the group consisting of imidazoles, imidazolines, oxadiazoles, oxazoles, oxazolines, isoxazoles, thiazoles, thiazolines, pyrrolines, pyridines, trihydropyrimidines, pyrazoles, triazoles, isothiazoles, tetrazoles, thiadiazoles, pyridazines, pyrazines, oxazines and dihydrooxazine. Preferred non-ionic promoters include those selected from the group having Formula (I) or Formula (II) as follows:

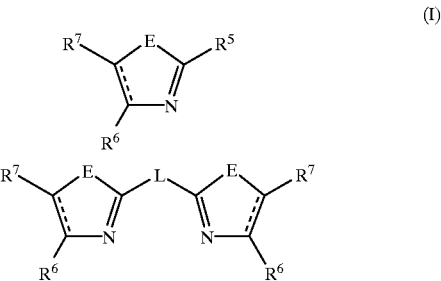

where E is selected from —O—, —S—, —Se—, —$CH_2$— and —$N(R^8)$—; $R^5$ is selected from the group consisting of $CH_3$ and $C_2H_5$ (and is preferably $CH_3$); $R^6$ and $R^7$ are selected from the group consisting of H, $CH_3$, $C_6H_5$ (i.e., phenyl), $CH_2C_6H_5$, $CH(CH_3)_2$, and fused phenyl; L is selected from the group consisting of —O—, —S—, —Se—, —$N(R^8)$—, —$C_6H_4$—, 2,6-pyridyl, —$OC_6H_4$—$C_6H_4O$—, —$CH_2CH_2OCH_2CH_2$— and —$(CH_2)_p$— where p is an integer from 0 to 6; and each $R^8$ is selected from the group consisting of H and $C_mH_{2m+1}$ where m is an integer from 1 to 6. The bond between each pair of carbon atoms respectively attached to $R^6$ and $R^7$ (as represented by the dashed bond lines in Formula (I) and Formula (H) can be either a single or a double bond. Of note are compounds of Formula (II) which are optically active.

Without wishing to be bound by theory, it is believed that the effect of the promoter(s) is to enhance the rate and selectivity of the reaction. Frequently, use of the promoter(s) will enable operation of the reaction at a lower temperature, and with an acceptable rate, than would be possible in the absence of the promoter. Reference is made to U.S. patent application Ser. No. 60/001,702 [CR-9788-P1] a priority document for U.S. Pat. No. 6,040,487, and U.S. patent application Ser. No. 60/019,994 [CR-9789-P3], which are hereby incorporated by reference, for further disclosure relating to promoters (see also International Application Nos. PCT/US96/12548 and PCT/US96/12547, respectively).

The process of this invention is carried out in the presence of a solvent. Typically, the solvents of this invention divide the reaction mixture into two liquid phases. Suitable solvents for the process of the invention thus include those which not only promote the formation of the 1:1 adduct, but also divide the reaction mixture into two liquid phases. The product addition compound is preferably concentrated in the lower liquid phase, while the solvent and catalyst are preferably concentrated in the top liquid phase. Preferred solvents for the process of this invention include dinitriles and cyclic carbonate esters. These solvents are commercially available. Examples of solvents for the process of this invention include ethylene carbonate, propylene carbonate, butylene carbonate, 1,2-cyclohexane carbonate, malononitrile, succinonitrile, ethyl succinonitrile, glutaronitrile, methyl glutaronitrile, adiponitrile, pimelonitrile, suberonitrile, and mixtures thereof. Preferred solvents for the process of the invention are adiponitrile, glutaronitrile, methyl glutaronitrile, and propylene carbonate.

The choice of the solvent for the process of the invention will require some experimentation, as the solubility characteristics of the starting materials and adducts need to be considered to develop the required two phase system. However, the preferred solvents noted above provide the desired two phase systems for a number of addition reactions as illustrated in the Examples.

Another important criterion for the choice of solvent is the boiling point of the solvent relative to that of the desired addition compounds. It is preferred that the boiling point of the solvent be higher than the boiling point of the adduct so that easy separation of the adduct from the solvent may be made by distillation.

Another important criterion for the choice of solvent is that it serve as a solvent for the catalyst or catalyst/promoter mixture at the reaction temperature or below.

The catalyst system comprising the copper(I) compound, the soluble halide promoter, and the solvent, can be prepared in advance in a suitable mixing vessel and then added to the reaction mixture. Alternatively, the individual components of the catalyst system can be added individually to the reactor.

The process of the present invention is suitably conducted at a temperature in the range of from about 90° C. to 150° C., preferably from about 100° C. to about 140° C., and most preferably, from about 110° C. to 130° C.

The pressure of the process is not critical and can be subatmospheric, atmospheric or superatmospheric, preferably, superatmospheric. The pressure in the system is frequently governed by the vapor pressures of the reactants at the temperature of the reaction. The reaction may be carried out under a pressure of nitrogen or other inert gas diluent.

While the use of a copper(I) catalyst tends to minimize the formation of higher telomers as known in the art, the formation of 2:1 and higher adducts (i.e., those addition compounds containing more than one mole of alkene per mole of adduct) can be further controlled by manipulating reaction variables such as the molar ratio of the halogenated alkane to the alkene. Higher molar ratios of halogenated alkane to alkene and dilution of the alkene reduce telomer formation. This can be accomplished by continuously feeding the alkene or mixture of the alkene and of the halogenated alkane to a heel of the halogenated alkane and catalyst mixture.

The total amount of copper(I) catalyst used in the reaction of this invention is typically at least about 5 mmoles, preferably from about 5 mmole to 700 mmoles, and more preferably from about 10 mmoles to 100 mmoles, per mole of alkene used.

The amount of ionic promoter used in the process of this invention is enough to provide about 0.25 to 3.0 mole of halide per gram-atom of copper(I), preferably about 1 mole of halide per gram-atom of copper(I). Use of more or less promoter will not provide the maximum benefit of the promoter.

When used, the amount of optional heterocyclic non-ionic promoter used in the reaction of this invention is typically at least an amount sufficient to provide 2 mmol of heterocyclic ring which contains carbon-nitrogen double bonding per mmol of copper catalyst. For example, typically at least about 2 moles of Formula (I) promoter or about 1 mole of Formula (II) promoter is typically used per mole of copper catalyst.

The amount of halogenated alkane used in the reaction of this invention is typically at least about 1 mole, and preferably from about 2 moles to 10 moles, per mole of alkene used.

The amount of solvent used in the reaction of this invention is typically at least about 5 moles, and preferably from about 10 moles to 100 moles, per mole of copper catalyst used.

The process of the present invention facilitates easy separation of the 1:1 addition product of the halogenated alkane to the alkene by taking advantage of the two phase nature of reaction mixture of this invention. That is, the desired 1:1 addition product tends to accumulate in the lower of the two liquid layers while the solvent and the catalyst tend to accumulate in the upper layer. The upper and lower layers may be separated continuously in a separation zone (e.g., a decanter) as is known in the art or on a batch basis by allowing the phases to separate in the reactor or a holding tank and removing the lower layer from the bottom of the vessel. The catalyst and solvent in the upper layer may be re-used for subsequent reactions. Since a small amount of solvent is dissolved in the lower layer and is removed with the product, it is desirable to replace lost solvent in a continuous process.

If the reaction is being operated in a continuous manner or if multiple batches are being run with the same catalyst charge, a gradual loss of reaction rate may be observed. A satisfactory reaction rate can be restored by addition of the optional promoter to the reaction.

The desired addition product may be separated from any alkene starting material, alkane starting material, solvent, and any higher telomer products by conventional techniques such as distillation. The low boiling fraction will typically be the starting halogenated alkane and the alkene which may be recovered and recycled to the reactor. Higher boiling material will comprise the solvent and any higher boiling telomer by-products. The higher boiling phase may be further refined and the solvent recycled to the reactor. The separation of the two liquid phases in the reactor may be done at temperatures between the reaction temperature and ambient temperature; cooling the reaction mixture lower than room temperature is usually not necessary.

The reaction zone and its associated feed lines, effluent lines and associated units should be constructed of materials resistant to corrosion. Typical materials of construction include steel reactors lined with poly(tetrafluoroethylene) or glass and glass reactors.

The addition compounds that comprise the products of this invention are useful as intermediates for the formation of hydrofluoroalkanes. These addition compounds can be reacted with hydrogen fluoride in either the liquid or vapor phase in the presence of a suitable fluorination catalyst.

In the liquid phase, the addition compounds can be reacted with HF in the presence of catalysts selected from the halides of antimony, molybdenum, niobium, tantalum, tin and titanium, and mixtures thereof, preferably, antimony, niobium and tantalum. The temperature of the reaction can be in the range of 50° C. to 175° C., preferably, 60° C. to 150° C. The pressure is selected so that the the reaction medium is maintained in the liquid state, typically between 101 kPa and 5000 kPa, preferably, 1135 kPa to 3203 kPa. For example, 1,1,1,3,3,3-hexachloropropane (HCC-230fa) can be reacted with HF in the liquid phase using halides, fluorosulfonates or triflates of antimony, molybdenum, niobium, tantalum, tin or titanium, or mixtures thereof as catalysts to produce 1,1,1,3,3,3-hexafluoropropane (HFC-236fa). 1-Chloro-1,1,3,3,3-pentafluoropropane (HCFC- 235fa) can also be prepared from HCC-230fa. HCFC-235fa can be hydrodechlorinated using a hydrodehalogenation catalyst to produce 1,1,1,3,3-pentafluoropropane (HFC-245fa). Palladium on acid-washed carbon is a preferred catalyst for the conversion of HCFC-235fa to HFC-245fa.

In another embodiment of this invention carbon tetrachloride can be reacted with vinyl chloride to produce the adduct 1,1,1,3,3-pentachloropropane (i.e., $CCl_3CH_2CHCl_2$ or HCC-240fa). $CCl_3CH_2CHCl_2$ can then be reacted with HF in the liquid phase using the process described above to produce $CF_3CH_2CHF_2$. The reaction products may be separated by conventional techniques such as distillation. Hydrofluorocarbons such as $CF_3CH_2CHF_2$ form azeotropes with HF; and conventional decantation/distillation may be employed if further purification of the hydrofluorocarbons is desired.

In the vapor phase, the addition compounds can be reacted with HF in the presence of catalysts comprising trivalent chromium. Catalysts prepared by pyrolysis of $(NH_4)_2Cr_2O_7$ to produce $Cr_2O_3$ and pretreated with HF and catalysts prepared by pretreating $Cr_2O_3$ having a surface area greater than about 200 m$^2$/g with HF are preferred. The temperature of the reaction can be in the range of 200° C. to 400° C., preferably, 250° C. to 375° C. The pressure is not critical and is selected so that the reaction starting materials and products are maintained in the vapor state at the operating temperature. For example, it has recently been disclosed in U.S. Pat. No. 5,414,165 that 1,1,1,3,3,3-hexafluoropropane may be prepared in high yield from 1,1,1,3,3,3-hexachloropropane by a vapor phase hydrofluorination process in the presence of a trivalent chromium catalyst.

Although the 1:1 addition compounds of the halogenated alkanes to the alkenes are the preferred products, the 2:1 adducts may also be useful intermediates.

Without further elaboration, it is believed that one skilled in the art can, using the preceding description, utilize the present invention to its fullest extent. The following specific embodiments are, therefore, to be construed as merely illustrative, and does not constrain the remainder of the disclosure in any way whatsoever.

EXAMPLES

Legend:
ADN is $CN(CH_2)_4CN$  VCl$_2$ is $CH_2$=$CCl_2$

Example 1

Preparation of 1,1,1,3,3,3-Hexachloropropane

A 400 mL Hastelloy™ C nickel alloy shaker tube was charged with anhydrous cuprous chloride (1.39 g, 0.014 mole), triethylamine hydrochloride (1.93 g, 0.014 mole), adiponitrile (52.0 g, 0.481 mole), carbon tetrachloride (151.0 g, 0.982 mole), and vinylidene chloride (47.5 g, 0.490 mole). The tube was sealed, cooled in a dry ice bath, evacuated, and purged with nitrogen several times. The tube was placed in a heating jacket and agitation begun. The tube was heated to 120° C. over the course of 1.3 hours and then held at 119–122° C. for one hour; during this time the pressure rose to a maximum of 83 psig (674 kPa) and then dropped to 41 psig (384 kPa) at the end of the heating period. The tube was then cooled to ambient temperature.

The tube was discharged to afford 244.9 g of a product consisting of a dark red brown liquid layer over a pale yellow lower liquid layer. The top layer (109.7 g) was filtered to yield 1.2 of solid. The top and bottom layers were analyzed by gas chromatography and found to have the compositions (in grams) indicated in Table 1 below.

TABLE 1

| | Weights of Components, g | |
|---|---|---|
| Component | Top Layer | Bottom Layer |
| ADN | 53.8 | 2.7 |
| VCl$_2$ | 0.1 | 0.2 |
| CCl$_4$ | 23.5 | 60.0 |
| CCl$_3$CH$_2$CCl$_3$ | 26.8 | 57.0 |
| CCl$_3$(CH$_2$CCl$_2$)$_2$Cl | 3.6 | 8.4 |
| CCl$_3$(CH$_2$CCl$_2$)$_3$Cl | — | 0.9 |

Examples 2–23

The reaction procedure for Examples 2–23 was similar to that of Example 1; the nominal reaction temperature and time was 120° C. and one hour, respectively. In each case, 0.98 mole $CCl_4$ and 0.49 mole $CH_2$=$CCl_2$ were reacted in the presence of 52.0 g of adiponitrile solvent and 0.014 mole of catalyst. Unless otherwise indicated, the amount of promoter is 0.014 mole. The % yield of $CCl_3CH_2CCl_3$ is based on the vinylidene chloride charged to the shaker tube. The $C_3$:$C_5$ ratio is the molar ratio of $CCl_3CH_2CCl_3$ to $CCl_3(CH_2CCl_2)_2Cl$ formed in the reaction.

TABLE 2

| Ex. No. | Catalyst | Promoter | CH$_2$=CCl$_2$ Conv. | % Yield CCl$_3$CH$_2$CCl$_3$ | C$_3$:C$_5$ Ratio |
|---|---|---|---|---|---|
| 2 | CuCl | None | 70.3 | 35.5 | 10.5 |
| 3 | CuCl | None | 72.0 | 31.6 | 13.2 |
| 4 | CuCl$_2$ | None | 73.2 | 30.2 | 8.4 |
| 5 | CuCl$_2$ | None | 69.8 | 29.5 | 9.6 |
| 6 | CuCl | KCl | 79.8 | 44.3 | 7.7 |
| 7 | CuCl | KBr | 71.3 | 34.8 | 7.6 |
| 8 | CuCl | KI | 87.3 | 16.1 | 2.0 |
| 9 | CuCl | KF | 67.4 | 38.5 | 10.4 |
| 10 | CuCl | [N(C$_4$H$_9$)$_4$]Br | 89.9 | 71.4 | 13.1 |
| 1$^a$ | CuCl | [NH(C$_2$H$_5$)$_3$]Cl | 99.2 | 68.3 | 9.7 |
| 11 | CuCl | [N(CH$_3$)$_4$]Br | 98.2 | 58.5 | 9.0 |
| 12 | CuCl | [N(C$_4$H$_9$)$_4$]Cl | 99.7 | 70.3 | 8.6 |
| 13$^b$ | CuCl | [N(C$_4$H$_9$)$_4$]Br | 98.8 | 59.8 | 6.1 |
| 14$^c$ | CuCl | [N(C$_4$H$_9$)$_4$]Br | 79.7 | 53.4 | 12.9 |
| 15$^d$ | CuCl | [NR$_3$(CH$_3$)]Cl | 99.4 | 73.6 | 9.9 |
| 16 | CuCl | [N(CH$_3$)$_4$]HF$_2$ | 58.8 | 16.8 | 11.6 |
| 17$^e$ | CuCl | [N(C$_4$H$_9$)$_4$]F | 53.1 | 13.8 | 16.5 |
| 18 | CuBr | [N(C$_4$H$_9$)$_4$]Br | 72.3 | 57.4 | 12.5 |
| 19 | CuBr | [N(C$_4$H$_9$)$_4$]Cl | 65.2 | 52.0 | 17.2 |
| 20 | CuCl | [P(C$_6$H$_5$)$_4$]Cl | 95.1 | 73.2 | 12.6 |
| 21 | CuCl | [N(C$_4$H$_9$)$_4$]BF$_4$ | 75.7 | 42.8 | 8.7 |
| 22 | CuCl2 | [N(C$_4$H$_9$)$_4$]Br | 68.6 | 32.3 | 12.0 |
| 23 | CuCl | [N(C$_2$H$_5$)$_4$]Br | 90.9 | 58.0 | 9.8 |

$^a$This run represents Example 1 above
$^b$0.007 mole [N(C$_4$H$_9$)$_4$]Br added.
$^c$0.028 mole [N(C$_4$H$_9$)$_4$]Br added
$^d$R = caprylyl; sold under the tradename "Aliquat" 336.
$^e$[N(C$_4$H$_9$)$_4$]F added as a trihydrate.

What is clamed is:

1. A liquid phase process for producing halogenated alkane adducts of the formula $CAR^1R^2CBR^3R^4$ wherein
$R^1$, $R^2$, $R^3$, and $R^4$ are each independently selected from the group consisting of H, Br, Cl, F, $C_1$–$C_6$ alkyl, CN, $CO_2CH_3$, $CH_2Cl$, and aryl, provided that when either $R^3$ or $R^4$ is selected from the group consisting of $C_3$–$C_6$ alkyl, CN, $CO_2CH_3$, $CH_2Cl$, and aryl, then $R^1$, $R^2$, and the other of $R^3$ and $R^4$ are H, and when $R^3$ and $R^4$ are selected from the group consisting of Cl, F, CH$_3$ and C$_2$H$_5$, then $R^1$ and $R^2$ are H, and when either $R^1$ or $R^2$ and either $R^3$ or $R^4$ are selected from the group consisting of Cl, F, CH$_3$ and C$_2$H$_5$, then the other of $R^1$ and $R^2$ and the other of $R^3$ and $R^4$ are H;

A is selected from the group consisting of $CX_3$, $CH_{3-a}X_a$, $C_nH_{(2n+1)-b}X_b$ and $CH_cX_{2-c}R$ where R is $C_nH_{(2n+1)-b}X_b$, each X is independently selected from the group consisting of Br, F, Cl and I, a is an integer from 0 to 3, n is an integer from 1 to 6, b is an integer from 1 to 2n+1, and c is an integer from 0 to 1;

and B is selected from the group consisting of Br, Cl and I; provided that (1) when A is $CX_3$ then only one of X is I, (2) when A is $CH_{3-a}X_a$, then each X is B, and a is 2 when B is Br or Cl, and a is an integer from 0 to 2 when B is I, and (3) when A is $C_nH_{(2n+1)-b}X_b$, then each X is independently selected from Cl and F, and B is I, comprising:

reacting a halogenated alkane of the formula AB with an olefin of the formula $CR^1R^2$=$CR^3R^4$ in dinitrile or cyclic carbonate ester solvent which divides the reaction mixture into two liquid phases and in the presence of a catalyst system containing (i) at least one catalyst comprising monovalent copper; and (ii) at least one ionic promoter selected from the group consisting of substituted ammonium halides, pyridinium and substituted pyridinium halides, and quaternary salts of the type $(MQ_4)Y$ where M is an element of Group VA of the Periodic Table, Q is a $C_1$–$C_{18}$ hydrocarbyl group, and Y is Cl, Br or I.

2. The process of claim 1 wherein AB is selected from the group consisting of $CCl_4$, $CBrCl_3$, $CCl_2FCCl_2F$, $CCl_3CClF_2$, $CCl_3CF_3$, $CCl_3CF_2CCl_3$, $CCl_3CF_2CF_3$, $CCl_3CH_2CCl_3$, $CCl_3CH_2CF_3$, $CCl_3CF_2CClF_2$, $CF_3I$, $CF_3CF_2I$, $CF_3CFICF_3$ and $CF_3CF_2CF_2I$.

3. The process of claim 2 wherein the olefin is selected from the group consisting of $CH_2$=$CH_2$, $CH_2$=$CHCl$, $CH_2$=$CHF$, $CHCl$=$CHCl$, $CH_2$=$CCl_2$, $CH_2$=$CF_2$, $CH_2$=$CHCH_3$, $CH_2$=$CHCH_2Cl$, and $CH_2$=$CHC_6H_5$.

4. The process of claim 1 when the copper catalyst is selected from the group consisting of copper(I) chloride, copper(I) bromide, copper(I) iodide, copper(I)acetate and copper(I) thiocyanate.

5. The process of claim 1 wherein the reaction is operated in a continuous manner.

6. The process of claim 1 wherein the solvent is selected from the group consisting of ethylene carbonate, propylene carbonate, butylene carbonate, 1,2-cyclohexane carbonate, malononitrile, succinonitrile, ethyl succinonitrile, glutaronitrile, methyl glutaronitrile, adiponitrile, pimelonitrile, suberonitrile, and mixtures thereof.

7. A process for producing a hydrofluoroalkane comprising:

(a) producing a halogenated alkane adduct by reacting AB and $CR^1R^2$=$CR^3R^4$ in accordance with the process of claim 1, provided that $R^1$, $R^2$, $R^3$ and $R^4$ are independently selected from H, $CH_3$, $C_2H_5$, Cl and F, B and X are Cl and at least one of AB and $CR^1R^2$=$CR^3R^4$ contains hydrogen; and (b) reacting the adduct produced in (a) with HF.

* * * * *